US009665264B1

(12) United States Patent
Janiak

(10) Patent No.: US 9,665,264 B1
(45) Date of Patent: May 30, 2017

(54) MEDICAL DATA DISPLAY SYSTEM GRAPHICAL USER INTERFACE

(71) Applicant: Draeger Medical Systems, Inc., Andover, MA (US)

(72) Inventor: Matthew Janiak, Hudson, NH (US)

(73) Assignee: Draeger Medical Systems, Inc., Andover, MA (US)

( * ) Notice: Subject to any disclaimer, the term of this patent is extended or adjusted under 35 U.S.C. 154(b) by 954 days.

(21) Appl. No.: 13/949,972

(22) Filed: Jul. 24, 2013

(51) Int. Cl.
| G06F 3/0481 | (2013.01) |
| G06F 3/0486 | (2013.01) |
| G06F 3/0488 | (2013.01) |
| G06F 3/01 | (2006.01) |

(52) U.S. Cl.
CPC ............ *G06F 3/0486* (2013.01); *G06F 3/017* (2013.01); *G06F 3/0488* (2013.01); *G06F 3/04812* (2013.01)

(58) Field of Classification Search
CPC .. G06F 3/017; G06F 3/04812; G06F 3/04842; G06F 3/0486; G06F 9/543; G06F 3/04847; G06F 3/04886; G09G 2340/0464; G09G 2340/0407; G09G 2340/0442
See application file for complete search history.

(56) References Cited

U.S. PATENT DOCUMENTS

| 2006/0149597 | A1* | 7/2006 | Powell | G01D 21/00 705/2 |
| 2011/0126157 | A1* | 5/2011 | Lee | G06F 3/0482 715/834 |
| 2011/0199389 | A1* | 8/2011 | Lu | G06F 3/017 345/619 |
| 2011/0296353 | A1* | 12/2011 | Ahmed | G06F 3/017 715/848 |
| 2012/0036435 | A1* | 2/2012 | Yang | G06F 3/0482 715/702 |
| 2013/0007671 | A1* | 1/2013 | Hammontree | G06F 17/30716 715/853 |
| 2013/0086527 | A1* | 4/2013 | Inkala | G06F 3/0484 715/825 |
| 2013/0151983 | A1* | 6/2013 | Lovitt | G06F 9/4443 715/745 |
| 2013/0271470 | A1* | 10/2013 | Moore | G06F 19/322 345/440.1 |

(Continued)

*Primary Examiner* — Steven Sax
(74) *Attorney, Agent, or Firm* — Jones Day

(57) ABSTRACT

A graphical user interface is rendered in a display having a touchscreen interface. The display forms part of a medical data display system utilizing data from at least one sensor monitoring one or more physiological parameters of a patient. The graphical user interface separately displays at least two waveforms derived from the at least one sensor. Thereafter, user-generated input is received via the touchscreen interface of the display that includes at least one gesture selecting a waveform at a first location and terminating at a second location within the graphical user interface. Subsequently, the selected waveform is moved from the first location to the second location within the graphical user interface based on the at least one gesture. Related apparatus, systems, techniques and articles are also described pertaining to the movement of components in a graphical user interface of a medical data display system.

26 Claims, 12 Drawing Sheets

(56) References Cited

U.S. PATENT DOCUMENTS

| | | | | |
|---|---|---|---|---|
| 2013/0275145 A1* | 10/2013 | Moore | ................ | G06F 19/3418 |
| | | | | 705/2 |
| 2013/0275152 A1* | 10/2013 | Moore | .................. | G06Q 10/10 |
| | | | | 705/3 |
| 2013/0328787 A1* | 12/2013 | Stearns | .................. | G06F 3/038 |
| | | | | 345/173 |
| 2014/0125600 A1* | 5/2014 | Meng | .................... | G06F 3/0488 |
| | | | | 345/173 |
| 2014/0240240 A1* | 8/2014 | Beck | .................... | G06F 3/0488 |
| | | | | 345/173 |
| 2014/0249854 A1* | 9/2014 | Moore | ................ | G06F 19/3487 |
| | | | | 705/3 |
| 2014/0331158 A1* | 11/2014 | Hicks | ................. | G06F 3/04883 |
| | | | | 715/769 |
| 2014/0351738 A1* | 11/2014 | Kokovidis | ........... | A61B 5/7445 |
| | | | | 715/771 |
| 2015/0029095 A1* | 1/2015 | Gomez | .................. | G06F 3/017 |
| | | | | 345/156 |

* cited by examiner

MEDICAL DATA DISPLAY SYSTEM GRAPHICAL USER INTERFACE

TECHNICAL FIELD

The subject matter described herein relates to a medical data display system (e.g., patient monitoring system, central monitoring system, etc.) graphical user interface that allows a user, via a touchscreen display, to rearrange or otherwise manipulate displayed components including waveforms and parameter boxes.

BACKGROUND

Medical data display systems such as patient monitoring systems play an important role in assessing and monitoring the well-being of patients receiving care (whether during a procedure or as part of recovery). Various vital signs such as ECG, basic arrhythmia, respiration, pulse rate, temperature, noninvasive blood pressure and SpO2 can be simultaneously displayed. Some of these vital signs are displayed as waveforms that have values which vary over time. In some cases, a caregiver may need to pay special attention to one of the waveforms.

SUMMARY

In one aspect, a graphical user interface is rendered in a display having a touchscreen interface. The display forms part of a medical data display system utilizing data from at least one sensor monitoring one or more physiological parameters of a patient. The graphical user interface separately displays at least two waveforms derived from the at least one sensor with each waveform having a temporal dimension extending along an x-axis and a value dimension extending along a y-axis. The values of the waveform vary over time. Thereafter, user-generated input is received via the touchscreen interface of the display that includes at least one gesture selecting a waveform at a first location and terminating at a second location within the graphical user interface. Subsequently, the selected waveform is moved from the first location to the second location within the graphical user interface based on the at least one gesture.

The at least one gesture can include selecting the selected waveform and dragging and dropping the selected waveform to or adjacent to the second location. The at least one gesture can include first tapping the selected waveform followed by second tapping the graphical user interface at or adjacent to the second location. The at least one gesture can include a multi-finger gesture in which multiple fingers are used to select the waveform and move the waveform from the first location to the second location.

The display can be integral with a housing of the medical data display system and/or it can be remote from a housing of the medical data display system. The display can include a tablet computer or a mobile communications device. The medical data display system can be a bedside patient monitoring system. The medical data display system can be a central monitoring system remote from the patient A visual appearance of the selected waveform can be temporarily changed after the user-generated input is received until such time that the location of the selected waveform is moved to the second location.

At least a portion of the waveforms can have corresponding parameter boxes that are displayed adjacent to the parameter boxes. The parameter box corresponding to the selected waveform can be moved from adjacent to the first location to adjacent to the second location within the graphical user interface based on the at least one gesture. In some variations, the parameter box corresponding to the selected waveform can be maintained at a position adjacent to the first location.

In another interrelated aspect, a graphical user interface is rendered in a display having a touchscreen interface. The display is part of a medical data display system utilizing data from at least one sensor monitoring one or more physiological parameters of a patient. The graphical user interface separately displays at least two waveforms derived from the at least one sensor. Each waveform has a temporal dimension extending along an x-axis and a value dimension extending along a y-axis and the values of the waveform vary over time. Next, user-generated input can be received via the touchscreen interface of the display that includes at least one gesture selecting at least one waveform. Subsequently, the graphical user interface is rendered to remove the selected at least one waveform. In some variations, a size of at least one other waveform can changed to accommodate the removal of the selected at least one waveform.

In a further interrelated aspect, a graphical user interface is rendered in a display having a touchscreen interface. The display forms part of a medical data display system utilizing data from at least one sensor monitoring one or more physiological parameters of a patient. The graphical user interface separately displays a plurality of components comprising: at least two waveforms and at least two corresponding parameter boxes. The at least two waveforms and the at least two parameter boxes display data derived from the at least one sensor. Each waveform has a temporal dimension extending along an x-axis and a value dimension extending along a y-axis and the values of the waveforms vary over time. Thereafter, user-generated input is received via the touchscreen interface of the display that includes at least one gesture selecting a component at a first location. In response, the selected component is moved from the first location to a second location within the graphical user interface based on the at least one gesture.

Medical data display systems are also described that utilize data from at least one sensor monitoring one or more physiological parameters of a patient. The medical data display systems include a display having a touch screen interface, at least one data processor, and memory storing instructions, which when executed by the at least one data processor, results in operations as described herein.

Computer program products are also described that comprise non-transitory computer readable media storing instructions, which when executed one or more data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many advantages. For example, the current subject matter provides enhanced usability with regard to the movement of various components displayed in a patient monitor graphical user interface including waveforms and parameter boxes.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Figure 1:
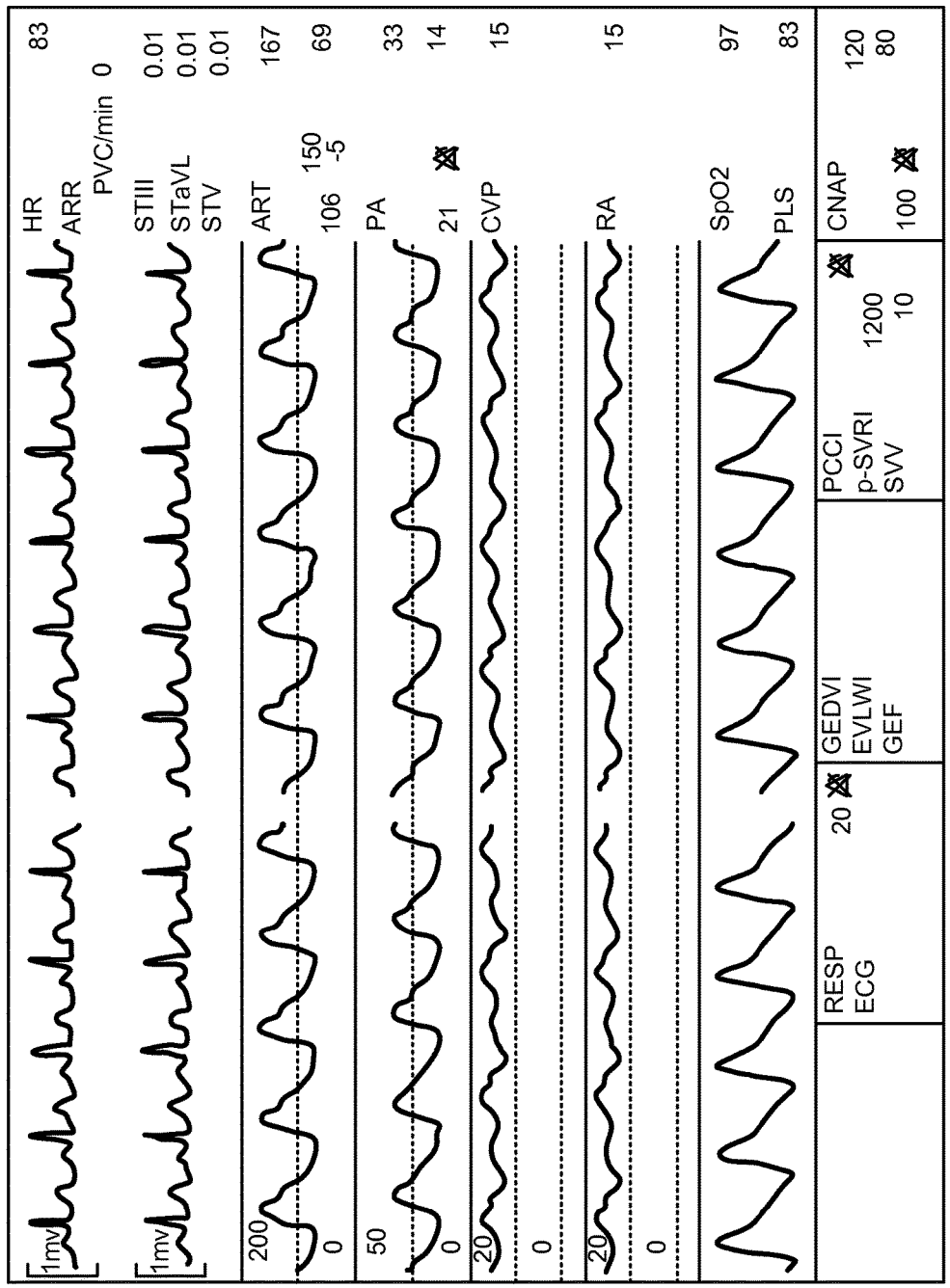
FIG. 1 is a system diagram showing a patient monitoring system.

FIG. 1 is a diagram 100 illustrating a patient monitoring system 110 having a display 120. The patient monitoring system 110 comprises at least one data processor and memory to store instructions for execution by the at least one data processor. In addition, the patient monitoring system 110 includes or can be coupled to at least one sensor 130. The at least one sensor 130 in turn is coupled to and monitors the wellbeing of a patient 140. As will be described in further detail below, the display 120 renders a graphical user interface with data characterizing measurements by the at least one sensor 130. The display 120 includes a touchscreen interface (e.g., a multi-touch tablet screen, etc.) that can enable a user 150 to modify how data is being presented in the display 120. The display 120 can be integrated with a device interfacing the sensor(s) 130 (e.g., a housing of the patient monitoring system 110) and/or it can comprise a tablet computer (e.g., IPAD, etc.) or mobile communications device which is portable and coupled to the sensor(s) via a wired or wireless network.

The sensor(s) 130 can comprise any type of sensor that can characterize a physiological parameter of the patient 140. Sample sensors 130 include, but are not limited to: ECG, basic arrhythmia, respiration, pulse rate, temperature, noninvasive blood pressure, and SpO2 sensors. Waveform, as used herein, describes any type of measurement which can vary over time and be presented with a varying value along a y-dimension.

Figure 2:
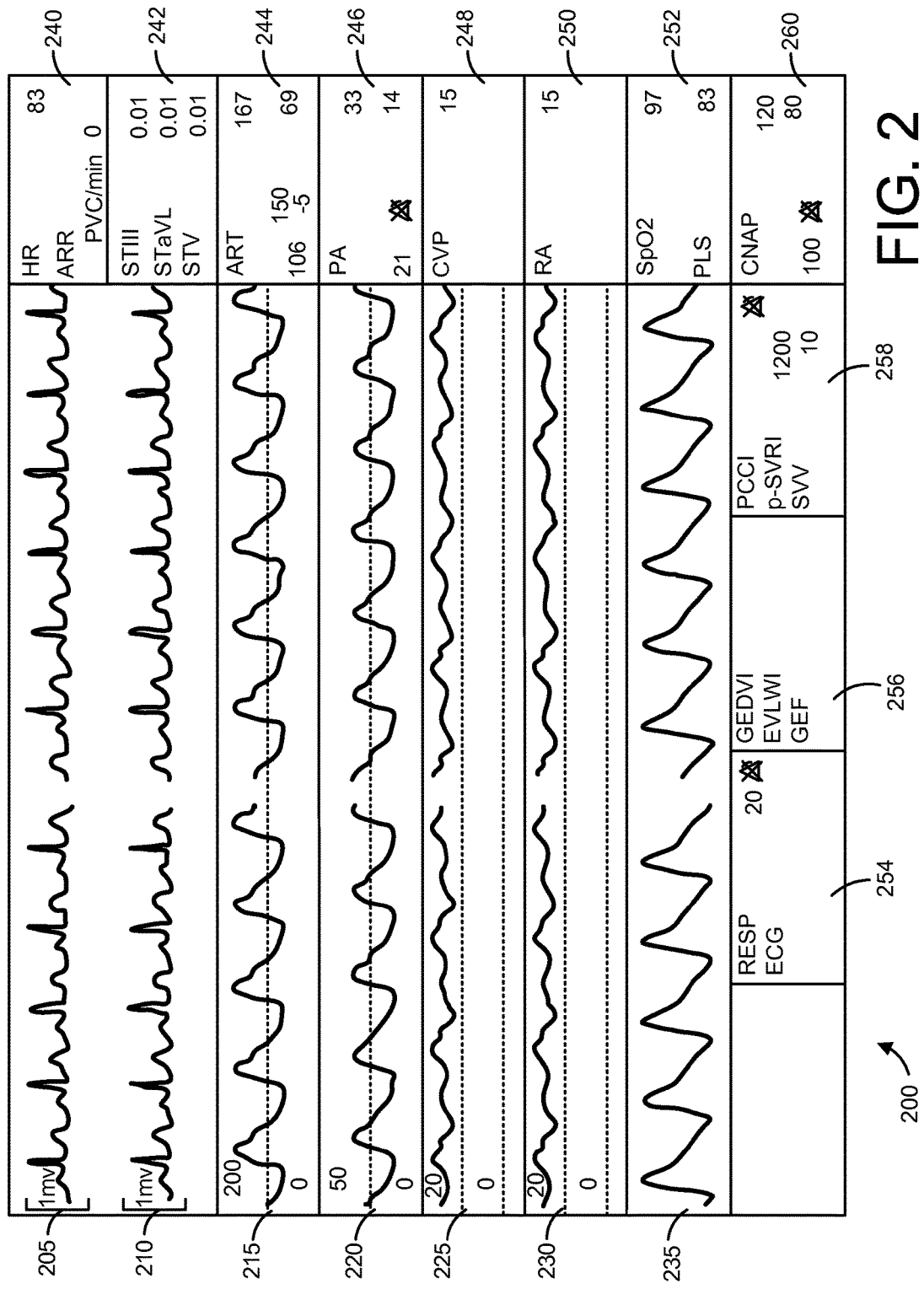
FIG. 2 is a first view of a graphical user interface of the patient monitoring system display.

The view 200 of FIG. 2 shows a plurality of waveforms 205-235 that each correspond to temporal measurements obtained from one or more physiological sensors coupled to or otherwise taking measurements from a patient and/or an environment in which a patient resides. In addition, the view 200 can include a plurality of parameter boxes 240-260 that also provide data relating to vital sign measurements of the patient. The graphical user interface can comprise one or more graphical user interface elements (which can be invisible from a user's perspective) that correspond to each of the waveforms 205-235 and, in some cases, the parameter boxes 240-260. For example, a user can, via the graphical user interface and the touchscreen interface display, activate the corresponding graphical user interface element(s) via one or more gestures.

With reference to FIGS. 2-10, waveform 205 characterizes a first ECG signal and the corresponding parameter box 240 includes related data including heart rate (HR), number of arrhythmias (ARR), and premature ventricular contractions per minute (PVC/min). Waveform 210 characterizes a second ECG signal and the corresponding parameter box 242 provides data regarding the ST segment of the ECG signal (i.e., the time period between the end of the ventricular depolarization and beginning of ventricular repolarization of the ventricular muscle). Waveform 215 characterizes arterial pressure and the corresponding parameter box 244 provides related numerical values. Waveform 220 characterizes pulmonary artery pressure and the corresponding parameter box 246 provides related numerical values. Waveform 225 characterizes a measurement of central venous pressure (CVP) and the corresponding parameter box 248 provides a numerical value for CVP. Waveform 230 characterizes respiratory rate (RA) with the corresponding parameter box 250 providing related numerical values. Waveform 235 is a plethysmograph with the corresponding parameter box 252 providing numerical pulse oximetry values. Other parameter boxes 254-260, can provide other numerical values based or otherwise derived from the waveforms 205-235 and/or from other sensors/data sources. It will be appreciated that other types of waveforms and parameter boxes can be additionally or alternatively be utilized depending on the particular condition/treatment of the patient.

As will be described in more detail below, a sequence of gestures can be used to rearrange components shown in the patient monitor graphical user interface including, without limitation, the waveforms 205-235 and the parameter boxes 240-260. The gesture sequences can include, for example, dragging and dropping the components (waveforms, parameter boxes) from a first location to a second location, flicking a component in a particular direction (which causes the other components to be re-arranged), tapping the components at a first location followed by tapping a second location (which results in the other component being moved to the second location). A single gesture can comprise the use of a single finger or it can comprise two or more fingers. A two finger gesture can be utilized to help avoid activating graphical user interface elements that are the result of a stray single finger touch (especially when intended for another purpose on the interface such as specifying a location to which a cursor and/or component should be moved) In addition, inactivity of a selected waveform after a certain period of time, such as 1 minute, can cause the view of the selected waveform to revert a default display setting. During a sequence of gestures, the views of the selected waveform can be continuously updated with new data acquired from the at least one sensor or it can remain static while new data is acquired from the at least one sensor.

Figure 3:
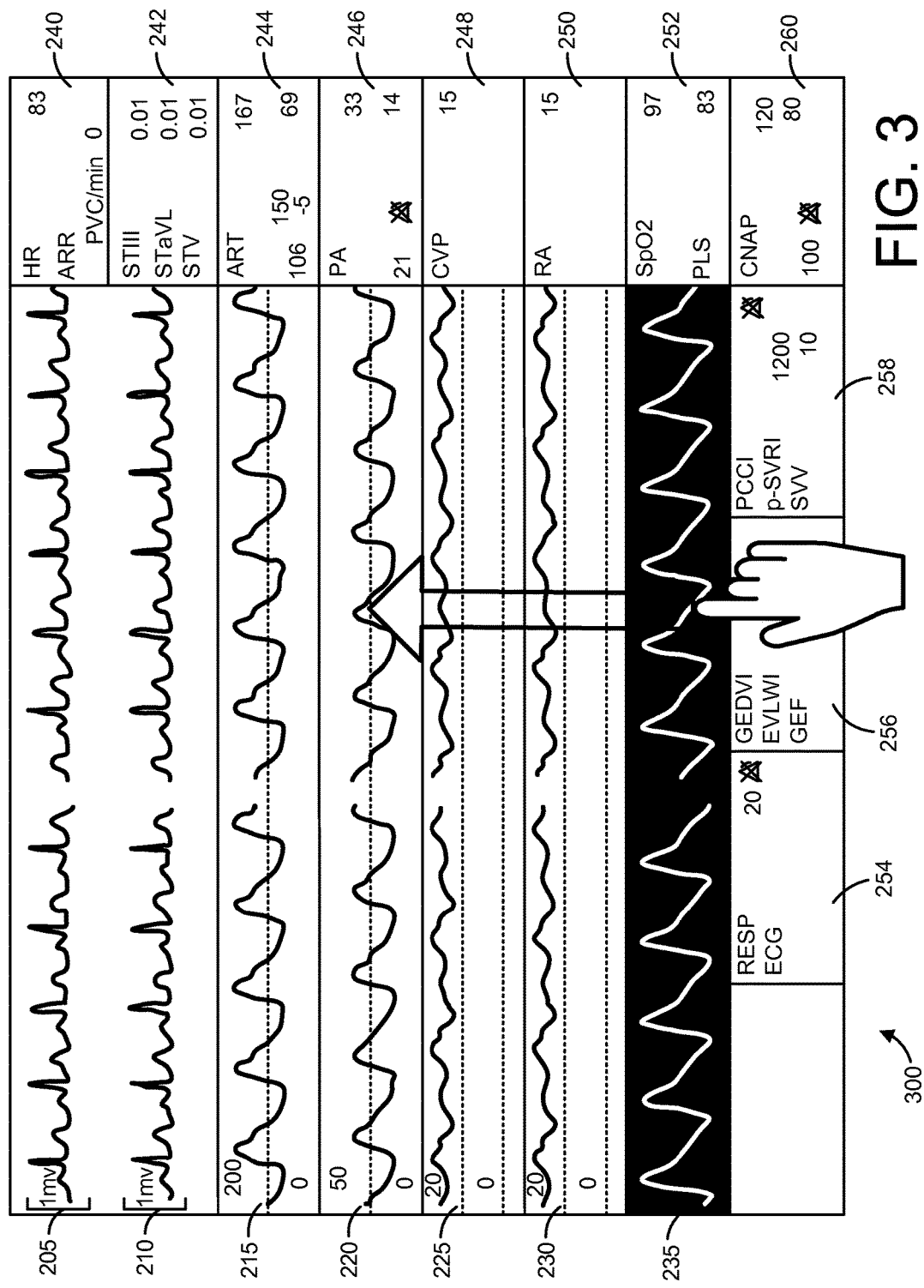
FIG. 3 is a second view of the graphical user interface of the patient monitoring system display.
Figure 4:
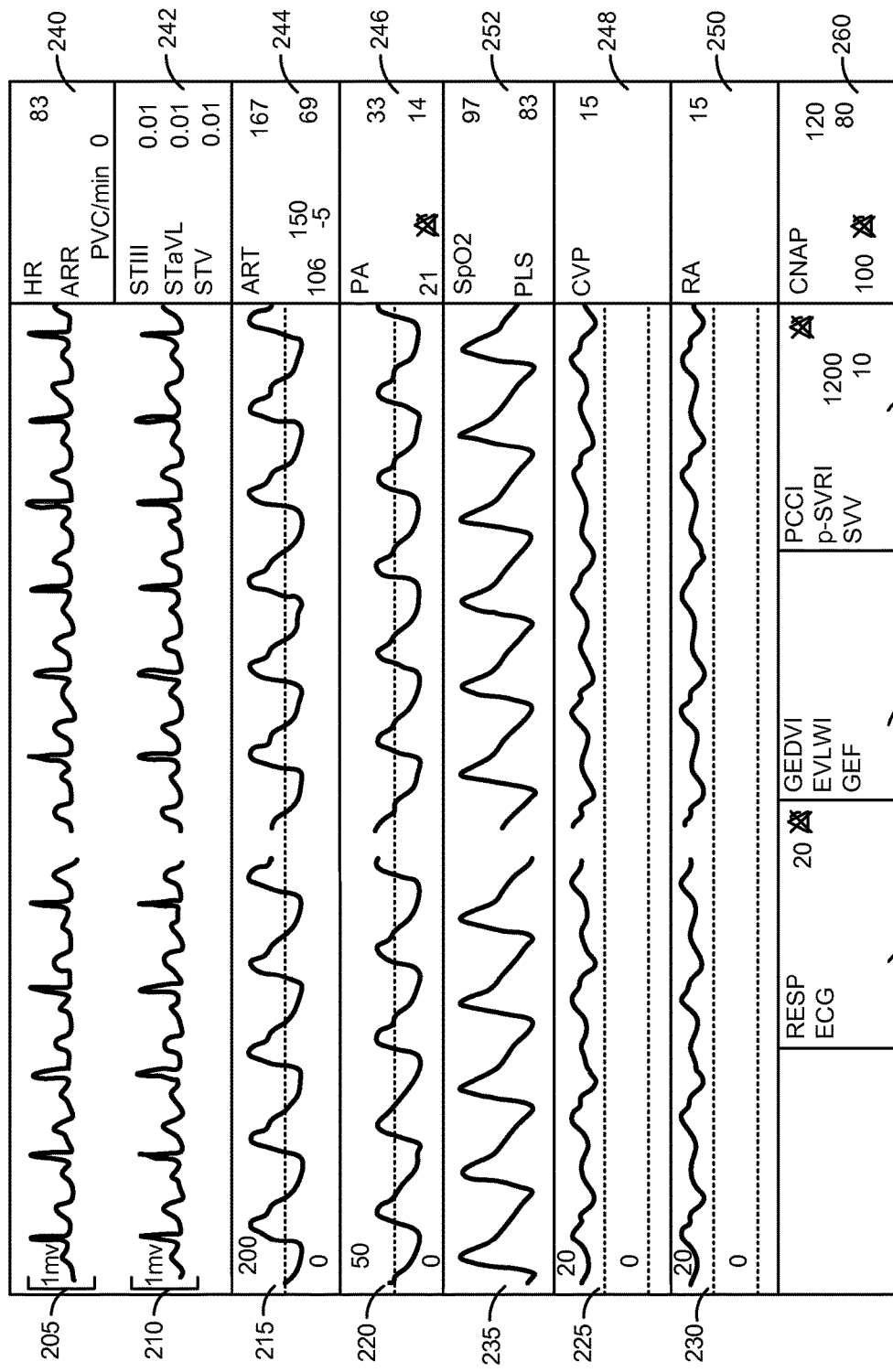
FIG. 4 is a third view of a graphical user interface of a patient monitoring system display.

With reference to diagram 300 of FIG. 3, the bottommost waveform 235 is selected via at least one gesture (via the touchscreen display) activating one or more graphical user interface elements that correspond to the waveform 270. In some variations, as illustrated, a visual appearance of the waveform 270 can be altered such as being highlighted and the like. The gesture(s) in this example involve the user sliding his finger(s) upwards to the row of waveform 220 (to activate a corresponding graphical user interface element). In some cases, the waveform 235 and the corresponding parameter box 252 move in real-time as the gesture advances upwards. Once the user has removed his finger(s) from the touchscreen display, with reference to diagram 400 of FIG. 4, the selected waveform 235 is advanced upwards to a position immediately below the row of waveform 220. In addition, the parameter box 252 that corresponds to the selected waveform 235 is also repositioned immediately below the row of waveform 220. While this sequence of gestures is a drag and drop arrangement, as noted above, other gesture sequences can be used.

Figure 5:
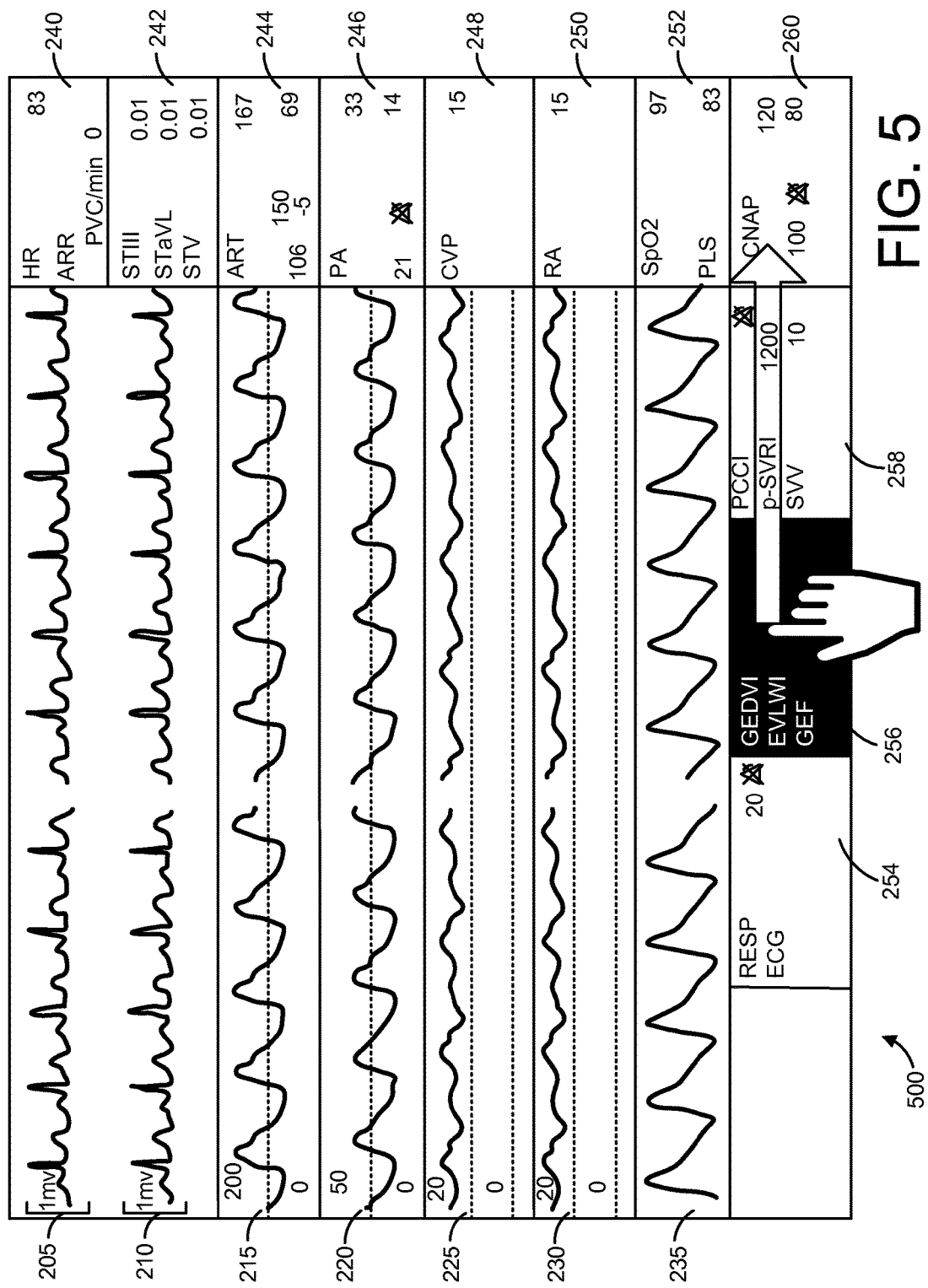
FIG. 5 is a fourth view of a graphical user interface of a patient monitoring system display.
Figure 6:
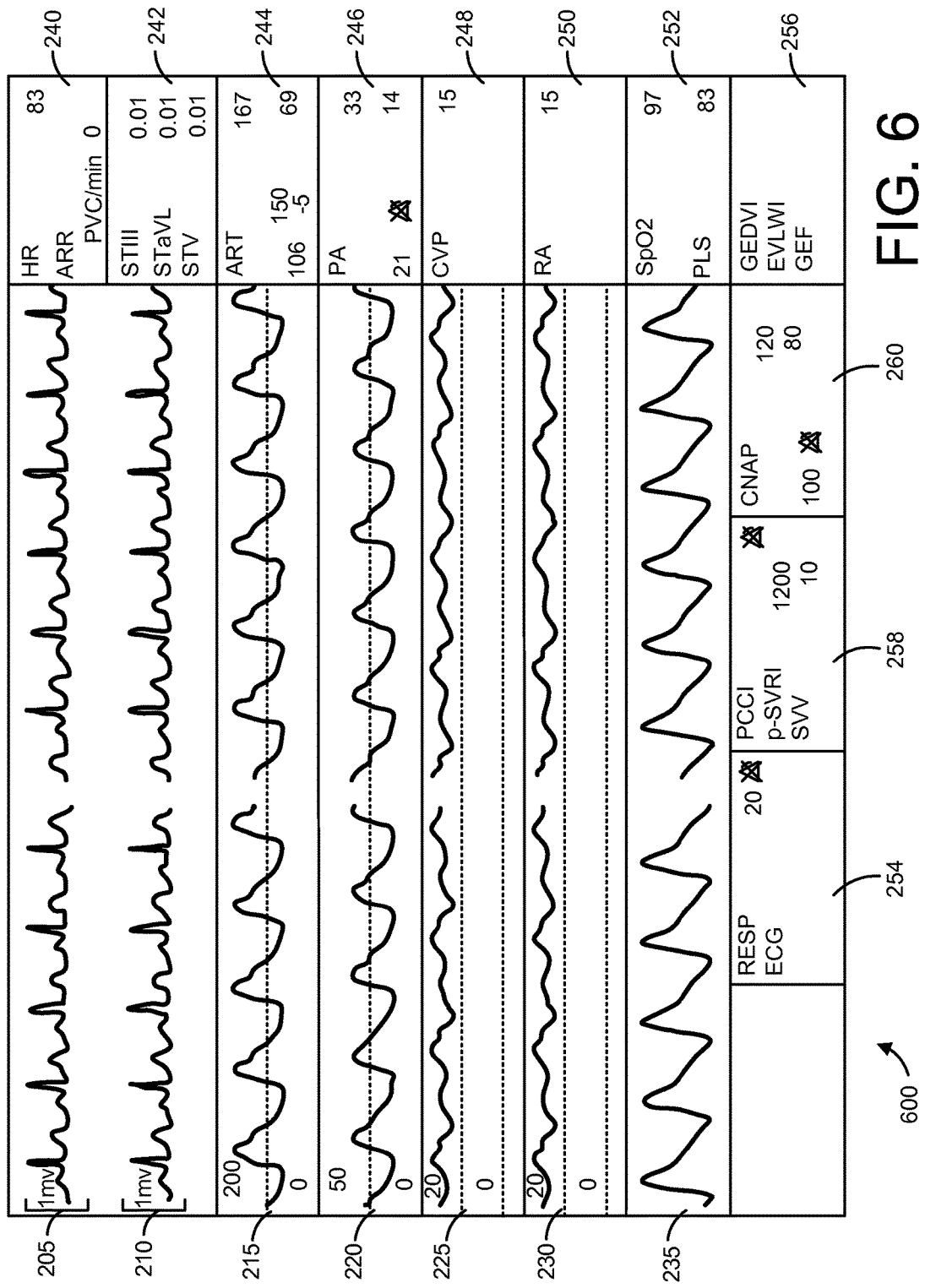
FIG. 6 is a fifth view of a graphical user interface of a patient monitoring system display.

With reference to diagram 500 of FIG. 5, a graphical user interface element corresponding to one of the parameter boxes 256 is activated using at least one gesture via the touchscreen display. The gesture(s) can include sliding the parameter box to parameter box 260. Once the gesture(s) is complete, with reference to diagram 600 of FIG. 6, the position of the parameter box 256 can replace the position of parameter box 260 causing parameter boxes 258, 260 to shift leftwards.

Figure 7:
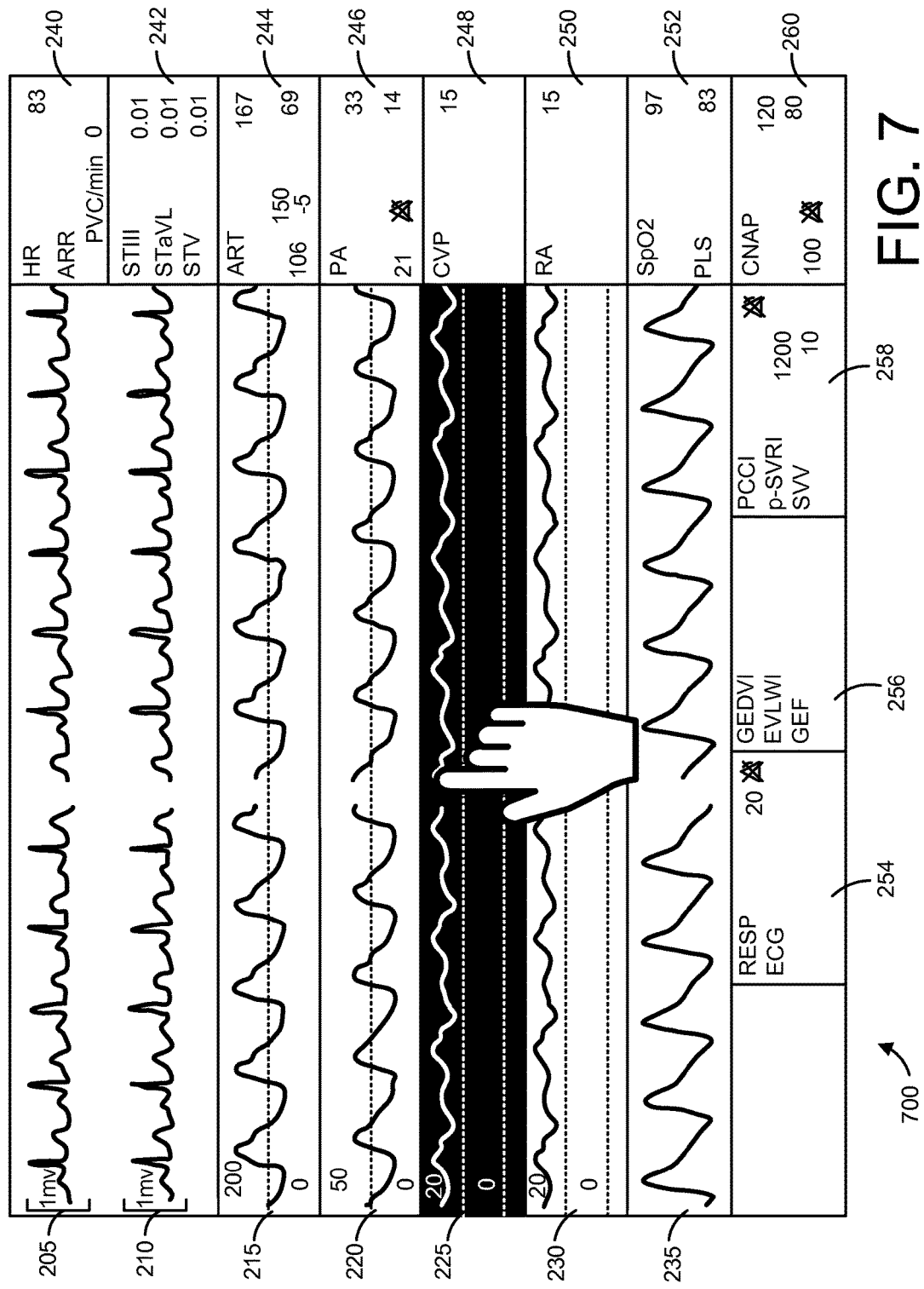
FIG. 7 is a sixth view of a graphical user interface of a patient monitoring system display.
Figure 8:
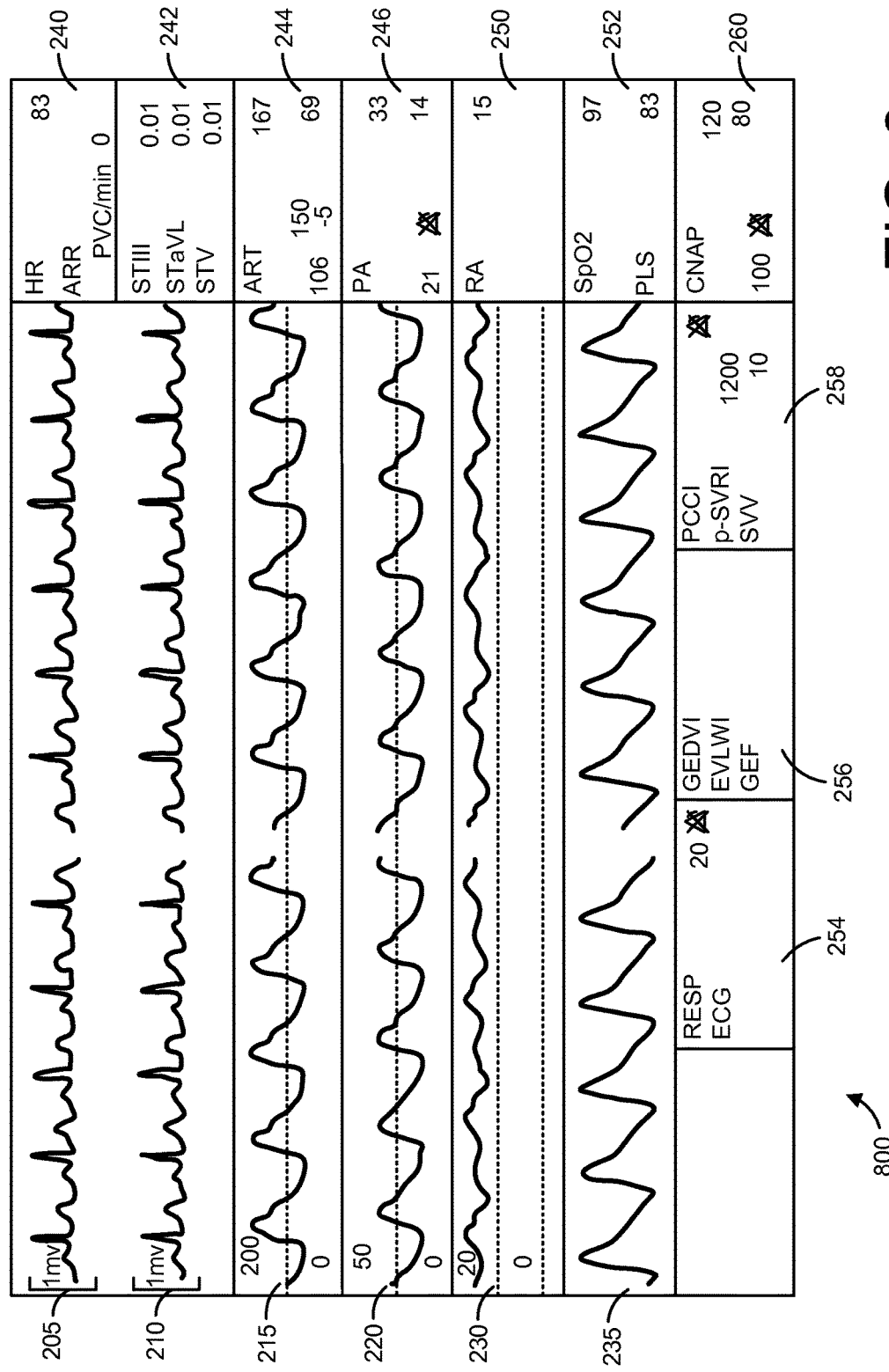
FIG. 8 is a seventh view of a graphical user interface of a patient monitoring system display.

With reference to diagram 700 of FIG. 7, a graphical user interface element corresponding to waveform 225 is activated using at least one gesture via the touchscreen display. The gesture(s) can include holding a finger over the waveform 225 for a pre-defined period of time (during which a visual appearance of the waveform 225 can be changed). Thereafter, with reference to diagram 800 of FIG. 8, waveform 225 and the corresponding parameter box 248 can be removed and, in some cases, the remaining waveforms 205-220, 230, 235. In some variations, the corresponding parameter box 248 can be maintained while the corresponding waveform 225 is removed and/or vice versa.

Figure 9:
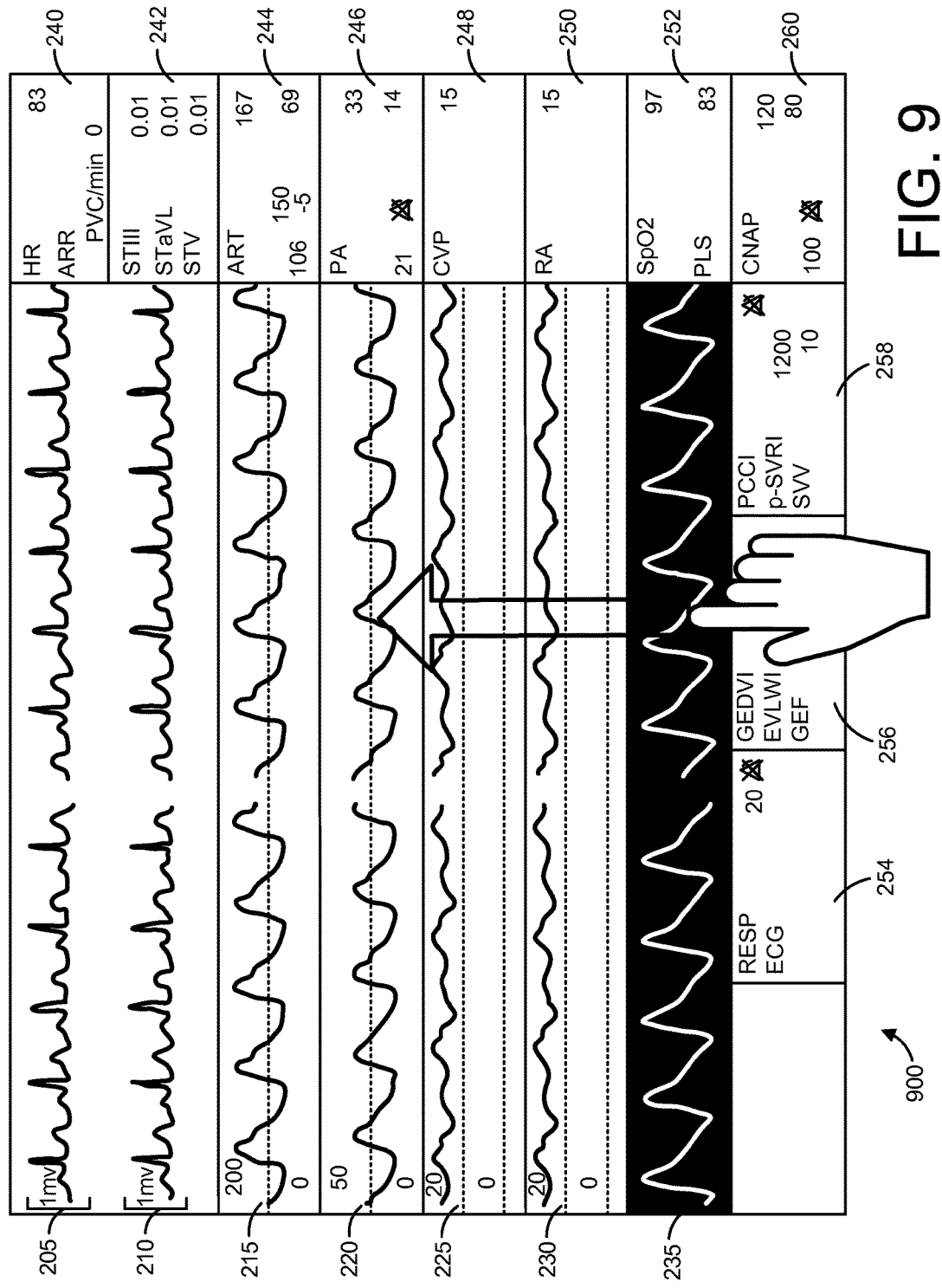
FIG. 9 is an eighth view of a graphical user interface of a patient monitoring system display.
Figure 10:
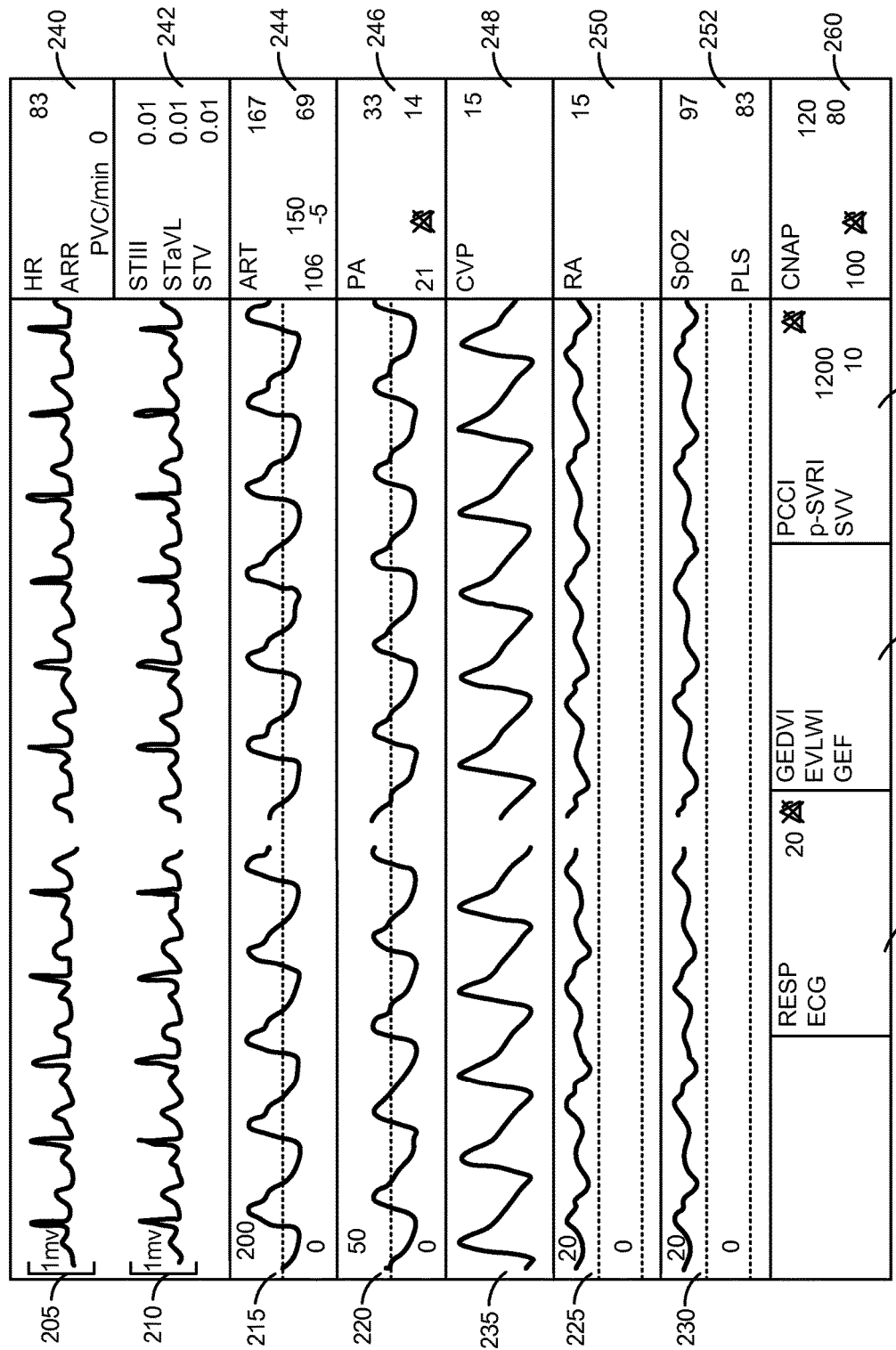
FIG. 10 is a tenth view of a graphical user interface of a patient monitoring system display.

With reference to diagram 900 of FIG. 9, a graphical user interface element corresponding to waveform 235 is activated using at least one gesture via the touchscreen display. Unlike the example of FIGS. 2 and 3, the result of the gesture(s) is that the waveform 235 is advanced upwards while the parameter box 252 remains in its original location (as shown in diagram 1000 of FIG. 10). Similarly, variations can be provided in which a parameter box remains in its original location when the corresponding waveform is removed altogether from the display, leaving a blank waveform area or being replaced by another different waveform.

It will be appreciated that the graphical user interface can also provide other functionality to allow for enhanced selection and/or arrangement of displayed components (e.g., waveforms, parameter boxes, etc.). For example, at least one gesture can be used to cause a drop down menu to be displayed that includes other components for display (which may or may not be already displayed in the graphical user interface). A flicking and/or scrolling gesture can be used to quickly rotate through different components (in some cases, the component/waveform is first selected by activating the corresponding graphical user interface element). For example, a waveform can be substituted in this manner with another waveform that is not currently being displayed. In some variations, the corresponding parameter box would also be displayed while in other variations the parameter box for the waveform that is being replaced continues to be displayed. The graphical user interface can also react in different fashions to the gesture(s) including bouncing back when an edge is received and/or a morphing visualization can be presented when changing an appearance and/or location of components.

Figure 11:
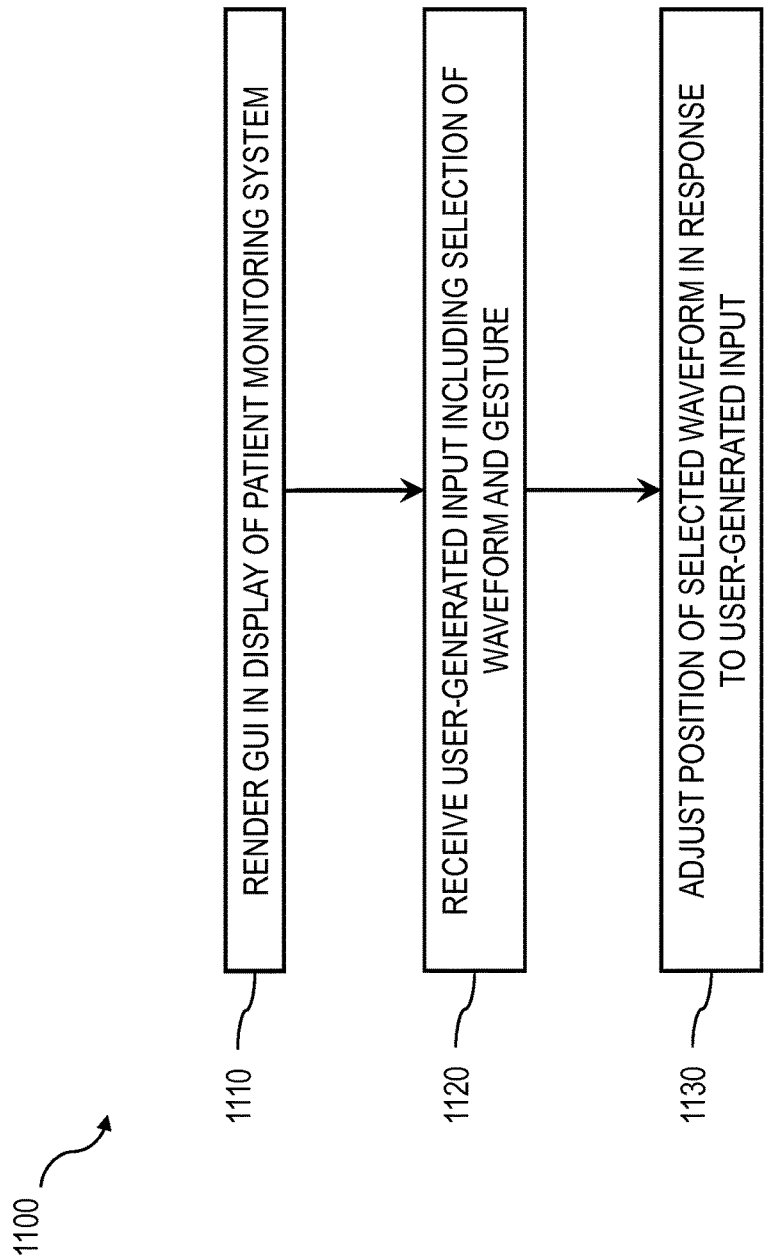
FIG. 11 is a first process flow diagram illustrating adjusting one or more displayed components of the graphical user interface of the patient monitoring system in response to one or more gestures.

FIG. 11 is a process flow diagram 1100 in which, at 1110, a graphical user interface is rendered in a display having a touchscreen interface. The display can be part of a medical data display system such a a bedside patient monitoring system or a remote central monitoring system. The medical data display system can utilize data from at least one sensor monitoring one or more physiological parameters of a patient. The graphical user interface separately displays at least two waveforms derived from the at least one sensor with each waveform having a temporal dimension extending along an x-axis and a value dimension extending along a y-axis, the values of the waveform varying over time. Subsequently, at 1120, user-generated input is received via the touchscreen interface of the display that includes at least one gesture selecting a waveform at a first location and terminating at a second location. Next, at 1130, the selected waveform is moved from the first location to the second location within the graphical user interface based on the at least one gesture.

Figure 12:
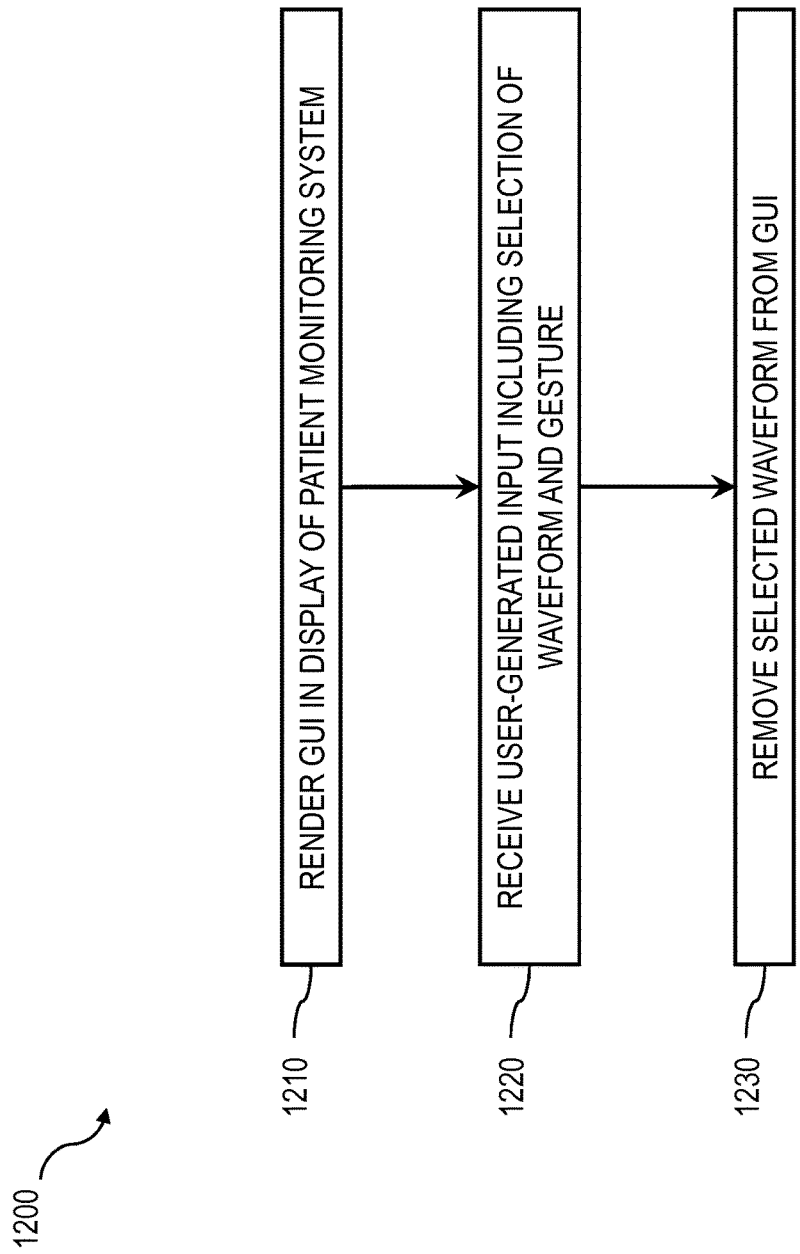
FIG. 12 is a second process flow diagram illustrating adjusting one or more displayed components of the graphical user interface of the patient monitoring system in response to one or more gestures.

FIG. 12 is a process flow diagram 1200 in which, at 1210, a graphical user interface is rendered in a display having a touchscreen interface. The display is part of a medical data display system that utilizes at least one sensor monitoring one or more physiological parameters of a patient. The graphical user interface separately displays at least two waveforms derived from the at least one sensor with each waveform having a temporal dimension extending along an x-axis and a value dimension extending along a y-axis, the values of the waveform varying over time. Thereafter, at 1220, user-generated input is received via the touchscreen interface of the display that includes at least one gesture selecting a waveform. Subsequently, at 1230, the graphical user interface is rendered to remove the selected waveform. In some variations, the remaining waveforms can be resized to fill in the space left by the removal of the selected waveform.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touchscreen, etc.), and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch-screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A computer-implemented method comprising:
   rendering a graphical user interface in a display having a touchscreen interface, the display being part of a medical data display system utilizing data from at least one sensor monitoring one or more physiological parameters of a patient, the graphical user interface separately and adjacently displaying in a list at least three different waveforms derived from at least one sensor, each waveform having a temporal dimension extending along an x-axis and a value dimension extending along a y-axis, the values of the waveform varying over time;
   receiving first user-generated input via the touchscreen interface of the display comprising at least one first gesture selecting a waveform at a first location in the list and terminating at a second location in the list within the graphical user interface;
   moving the selected waveform from the first location to the second location within the graphical user interface based on the at least one first gesture and changing a position of at least one other waveform to accommodate the movement of the selected waveform; and
   receiving second user-generated input via the touchscreen interface of the display comprising at least one second gesture being applied to the selected waveform at the second location within the graphical user interface, the at least one second gesture being different from the at least one first gesture;
   determining a type of the at least one second gesture; and
   wherein, based on the determined type of the at least one second gesture, the selected waveform is either continually updated with new data acquired from the at least one sensor or the waveform remains static while new data is acquired from the at least one sensor.

2. A method as in claim 1, wherein the at least one first gesture comprises selecting the selected waveform and dragging and dropping the selected waveform to or adjacent to the second location.

3. A method as in claim 1, wherein the at least one first gesture comprises first tapping the selected waveform followed by second tapping the graphical user interface at or adjacent to the second location.

4. A method as in claim 1, wherein the at least one first gesture comprises a multi-finger gesture in which multiple fingers are used to select the waveform and move the waveform from the first location to the second location.

5. A method as in claim 1, wherein the display is integral with a housing of the medical data display system.

6. A method as in claim 1, wherein the display is remote from a housing of the medical data display system.

7. A method as in claim 6, wherein the display comprises a tablet computer or a mobile communications device.

8. A method as in claim 1, wherein the medical data display system is a bedside patient monitoring system.

9. A method as in claim 1, wherein the medical data display system is a central monitoring system remote from the patient.

10. A method as in claim 1, further comprising: temporarily changing a visual appearance of the selected waveform after the user-generated input is received until the location of the selected waveform is moved to the second location.

11. A method as in claim 1, wherein at least a portion of the waveforms have corresponding parameter boxes that are displayed adjacent thereto.

12. A method as in claim 11, further comprising:
moving the parameter box corresponding to the selected waveform from adjacent to the first location to adjacent to the second location within the graphical user interface based on the at least one first gesture or the at least one second gesture.

13. A method as in claim 11, further comprising:
maintaining the parameter box corresponding to the selected waveform at a position adjacent to the first location.

14. A system comprising:
at least one data processor; and
memory storing instructions which, when executed by the at least one data processor, result in operations comprising:
rendering a graphical user interface in a display having a touchscreen interface, the display being part of a medical data display system utilizing data from at least one sensor monitoring one or more physiological parameters of a patient, the graphical user interface separately and adjacently displaying in a list at least three different waveforms derived from at least one sensor, each waveform having a temporal dimension extending along an x-axis and a value dimension extending along a y-axis, the values of the waveform varying over time;
receiving first user-generated input via the touchscreen interface of the display comprising at least one first gesture selecting a waveform at a first location in the list and terminating at a second location in the list within the graphical user interface;
moving the selected waveform from the first location to the second location within the graphical user interface based on the at least one first gesture and changing a position of at least one other waveform to accommodate the movement of the selected waveform; and
receiving second user-generated input via the touchscreen interface of the display comprising at least one second gesture being applied to the selected waveform at the second location within the graphical user interface, the at least one second gesture being different from the at least one first gesture;
determining a type of the at least one second gesture; and
wherein, based on the determined type of the at least one second gesture, the selected waveform is either continually updated with new data acquired from the at least one sensor or the waveform remains static while new data is acquired from the at least one sensor.

15. A system as in claim 14, wherein one of the at least one first gesture comprises selecting the selected waveform and dragging and dropping the selected waveform to or adjacent to the second location.

16. A system as in claim 14, wherein one of the at least one first gesture and comprises first tapping the selected waveform followed by second tapping the graphical user interface at or adjacent to the second location.

17. A system as in claim 14, wherein one of the at least one first gesture comprises a multi-finger gesture in which multiple fingers are used to select the waveform and move the waveform from the first location to the second location.

18. A system as in claim 14, wherein the display is integral with a housing of the medical data display system.

19. A system as in claim 14, wherein the display is remote from a housing of the medical data display system.

20. A system as in claim 19, wherein the display comprises a tablet computer or a mobile communications device.

21. A system as in claim 14, wherein the medical data display system is a bedside patient monitoring system.

22. A system as in claim 14, wherein the medical data display system is a central monitoring system remote from the patient.

23. A system as in claim 14, wherein the operations further comprise:
temporarily changing a visual appearance of the selected waveform after the user-generated input is received until the location of the selected waveform is moved to the second location.

24. A system as in claim 14, wherein at least a portion of the waveforms have corresponding parameter boxes that are displayed adjacent thereto.

25. A system as in claim 24, wherein the operations further comprise:
moving the parameter box corresponding to the selected waveform from adjacent to the first location to adjacent to the second location within the graphical user interface based on the at least one first gesture or the at least one second gesture.

26. A system as in claim 24, wherein the operations further comprise:
maintaining the parameter box corresponding to the selected waveform at a position adjacent to the first location.

* * * * *